United States Patent [19]

Bhasin

[11] 4,235,801
[45] Nov. 25, 1980

[54] PROCESS FOR PRODUCING ETHANOL FROM SYNTHESIS GAS

[75] Inventor: Madan M. Bhasin, Charleston, W. Va.

[73] Assignee: Union Carbide Corporation, New York, N.Y.

[21] Appl. No.: 676,129

[22] Filed: Apr. 12, 1976

Related U.S. Application Data

[63] Continuation of Ser. No. 541,660, Jan. 16, 1975, abandoned, which is a continuation-in-part of Ser. No. 437,141, Jan. 28, 1974, abandoned.

[51] Int. Cl.$^3$ .............................................. C07C 27/06
[52] U.S. Cl. ............................................ 260/449.6 R
[58] Field of Search ........................... 260/449.6, 449.5

[56] References Cited

PUBLICATIONS

Fischer et al, "Brennstoff Chemie", 17, 265–284 (1925).
Fischer et al, "Brennstoff Chemie", 16, 466 (1935).
Pichler, "Brennstoff Chemie", 19, 226 (1939).
Kratel, Doetoral Dissertation, Tech. University of Berlin–Charlottenburg (1937).
Eidus et al, lquest. Akad. Navk, SSSR, Ser. Khim. 7, 1160–1169 (1963).
Schultz et al, Bureau of Mines Report No. 6974.

*Primary Examiner*—Alan Siegel
*Attorney, Agent, or Firm*—Bernard Lieberman

[57] ABSTRACT

A process for the selective preparation of ethanol by continuously contacting a synthesis gas reaction mixture containing hydrogen and carbon monoxide with a rhodium-iron catalyst.

6 Claims, No Drawings

PROCESS FOR PRODUCING ETHANOL FROM SYNTHESIS GAS

CROSS-REFERENCE TO RELATED APPLICATIONS

This application is a continuation of our prior U.S. application: Ser. No. 541,660, filed Jan. 16, 1975, now abandoned, which is a continuation-in-part of application Ser. No. 437,141, filed Jan. 28, 1974, now abandoned and is related to application Ser. No. 541,661, filed Jan. 16, 1975, now abandoned.

BACKGROUND

This invention concerns the selective preparation of ethanol from synthesis gas. More particularly, the invention concerns reaction of carbon monoxide and hydrogen in the presence of a product-specific catalyst to produce ethanol.

The preparation of hydrocarbons and oxygenated hydrocarbons from synthesis gas (essentially a mixture of carbon monoxide with varying amounts of carbon dioxide, and hydrogen), has received extensive study and has achieved commercial adoption. Reaction conditions generally involve temperatures on the order of 150°–450° C., pressures of from atmospheric to about 10,000 psig, and hydrogen-to-carbon monoxide ratios in the range of 4:1 to about 1:4 with an iron group, mixtures of metal oxides, or a noble metal group hydrogenation catalyst.

One serious disability of most synthesis gas processes has been the non-selective or non-specific nature of the product distribution. Catalysts which possess acceptable activity generally tend to give a wide spectrum of products—hydrocarbons and oxygenated hydrocarbons—having a broad distribution of carbon atom contents. This not only complicates the recovery of desired products, but results in the wastage of reactants to commercially uninteresting byproducts.

In copending application Ser. No. 541,661 and in its parent Ser. No. 437,141, there has been described a process for the selective preparation of two-carbon atom oxygenated hydrocarbons, namely acetic acid, ethanol, and acetaldehyde, using a rhodium catalyst. It has now been discovered that it is possible to double selectivity toward ethanol, significantly reduce the formation of acetaldehyde and acetic acid, and retain the selectivity toward two-carbon atom oxygenated compounds.

SUMMARY OF INVENTION

Briefly, in accordance with the invention, a process is provided for the reaction of a synthesis gas containing carbon monoxide and hydrogen to prepare ethanol, by continuously contacting the gas with a catalyst essentially comprising rhodium and iron under suitable reaction conditions to form a substantial proportion of ethanol.

The reaction is conducted at more or less conventional reactive conditions of temperature, pressure, gas composition, and space velocity. At optimum reaction conditions there is little conversion to three carbon atom and higher hydrocarbons and oxygenated hydrocarbons; acetaldehyde and acetic acid are relatively minor products; and conversion to methane and methanol may readily be minimized. Thus, a reaction product stream is obtained from the reactor which contains a substantial proportion of ethanol.

DETAILED DESCRIPTION

In keeping with the invention, a synthesis gas containing carbon monoxide and hydrogen is contacted with a catalyst containing rhodium-iron under reactive conditions of temperature, pressure, gas composition, and, as an optional feature, space velocity to form a substantial proportion of ethanol in the reaction product stream. Overall, the reaction is conducted at reactive conditions of temperature, pressure, gas composition, and, as an optional feature, space velocity which are correlated so as to collectively produce acetic acid, ethanol, and/or acetaldehyde in an amount which is at least about 50 weight percent, preferably at least about 75%, of the two and more carbon atom compounds obtained by the reaction, and of those collective reaction products (that is, acetic acid, ethanol and acetaldehyde) the mole percent of ethanol produced is typically at least 25% of the total moles of such products, preferably at least 50 mole percent. The selectivity to the aforementioned two carbon products is invariably at least about 10%, and is usually upwards of about 25%; under the preferred conditions it exceeds 50% and, under optimum conditions, has reached 90% or more. Selectivity, or efficiency, is defined herein as the percentage of carbon atoms converted from carbon monoxide to a specified compound or compounds other than carbon dioxide.

As noted earlier, the reactive conditions of temperature, pressure, and gas composition are essentially conventional for synthesis gas conversions. Thus, existing technology and, in some instances, existing equipment may be used to effect the reaction.

The reaction is highly exothermic, with both the thermodynamic equilibria and the kinetic reaction rates being governed by the reaction temperature. Average catalyst bed temperatures are usually within the range of about 150°–450° C., but for optimum commercial conversions are within the range of about 200°–400° C., for example 250°–350° C.

The reaction temperature is an important process variable, affecting not only total productivity but selectivity toward the desired ethanol product. Over relatively narrow temperature ranges, as for example 10° or 20° C., an increase in temperature may somewhat increase total synthesis gas conversion, tending to increase the efficiency of ethanol production but decreasing the production of acetic acid. At the same time, however, higher temperatures favor methane production, and apparently methane production increases much more rapidly at higher temperatures than do conversions to the two carbon atom products. Thus, for a given catalyst and with all other variables held constant, the optimum temperature will depend more on product and process economics than on thermodynamic or kinetic considerations, with higher temperatures tending to increase the production of the two-carbon compounds, particularly ethanol, but increasing to an even greater extent the co-production of methane.

In the discussions above the indicated temperatures are expressed as average, or mean, reaction bed temperatures. Because of the highly exothermic nature of the reaction, the temperature should be closely controlled so as not to produce a runaway methanation, in which methane formation is increased with higher temperature, and the resulting exotherm increases the temperature further. To accomplish this, conventional temperature control techniques are utilized, as for example the use of fluidized bed reaction zones, the use of multistage fixed bed adiabatic reactors with interstage cooling, interstage injection of cool gas, or relatively small (1/16th inch or less) catalyst particles placed in tube-and-shell type reactors with a coolant fluid surrounding the catalyst-filled tubes.

The reaction zone pressure is desirably within the range of about 15 psig to about 10,000 psig, economically within the range of about 300–5,000 psig. Higher reaction zone pressures increase the total weight of product obtained per unit time and likewise improve the selectivity toward two carbon atom compounds.

The ratio of hydrogen to carbon monoxide in the synthesis gas may vary widely. Normally the mole ratio of hydrogen to carbon monoxide used in this invention is within the range of 20:1 to 1:20, or preferably within the range of about 5:1 to about 1:5. In most of the experimental work reported herein the mole ratio of hydrogen to carbon monoxide is somewhat less than 1:1. Increasing the ratio tends to increase the total rate of reaction, sometimes quite significantly, and has a small but favorable effect on production of two carbon atom products, but concurrently increases selectivity to methane. Increasing the hydrogen to carbon monoxide ratio also favors the formation of more highly reduced products, that is, ethanol rather than acetaldehyde or acetic acid.

Impurities in the synthesis gas may or may not have an effect on the reaction, depending on their nature and concentration. Carbon dioxide, normally present in an amount of up to about 10 mole percent, has essentially no effect. If a recycle operation is conducted, in which all or part of the reacted gas is recycled to the catalyst zone, precautions are desirably taken to remove oxygenated hydrocarbons before recycling.

One of the features of the present invention is the recognition that a low conversion—preferably less than 20% of the CO—favors the formation or production of a substantial proportion of acetic acid, ethanol and/or acetaldehyde, generally in excess of 10% as compared with a maximum of 3.4% in the prior art. This conversion is conveniently achieved by employing a high space velocity correlated with other reaction variables (e.g. temperature, pressure, gas composition, catalyst, etc.). Space velocities in excess of about $10^3$ gas hourly space velocity (volumes of reactant gas, at 0° C. and 760 mm mercury pressure, per volume of catalysts per hour) are generally employed, although it is preferable that the space velocity be within the range of about $10^4$ to about $10^6$ per hour. Excessively high space velocities result in an uneconomically low conversion, while excessively low space velocities cause the production of a more diverse spectrum of reaction products, including higher boiling hydrocarbons and oxygenated hydrocarbons.

The catalyst of rhodium and iron is provided in the reaction zone by a number of techniques, or a combination of a number of these techniques. One technique is to coat the reaction zone (or reactor) walls with a combination of rhodium and iron. Another is to coat a porous screen or screens with a thin coating of a combination (or mixture) of both. Still another way involves placing particles of a combination of rhodium and iron in the reaction zone, generally supported by an inert porous packing material. Another way is to deposit rhodium and iron onto a particulate support material and place the supported rhodium into the reaction zone. Any combination of these techniques can be employed.

However, important advantages within the scope of the invention are achieved when the rhodium metal and the iron are in a highly dispersed form on a particulate support. On the basis of experience to date the amount of each of the rhodium and iron on the support should range from about 0.01 weight percent to about 25 weight percent, based on the combined weight of the metals and the support material. Preferably, the amount of each is within the range of about 0.1 to about 10 weight percent.

A wide variety of support materials has been tested. A relatively high surface area particulate support, e.g. one having a surface area upwards of about 1.0 square meters per gram (BET low temperature nitrogen adsorption isotherm method), is preferred, desirably upwards of about 1.5 square meters per gram, although surface area alone is not the sole determinative variable. Based on research to date, silica gel is preferred as the catalyst base or support, with alpha alumina, magnesia, eta alumina, gamma alumina, and active carbon being progressively less desirable. Zeolitic molecular sieves, primarily the higher silica-to-alumina crystalline zeolites, also have promise.

The rhodium and the iron may be deposited onto the base or support by any of the techniques commonly used for catalyst preparation, as for example impregnation from an organic or inorganic solution, precipitation, coprecipitation, or cation exchange. Conveniently, a solution of a decomposable or reducible inorganic or organic rhodium compound and an iron compound is appropriately contacted with the support material, and the support then dried and heated, the latter advantageously under reducing conditions, to form the finely dispersed rhodium-iron catalyst. The rhodium and the iron may be deposited concurrently or sequentially.

The invention in its various aspects is illustrated in the different "Series" of experiments presented below. In each instance it will be appreciated that the tests are exemplary only, and are not intended to be wholly definitive or exclusive with respect to scope or conditions of the invention.

SERIES A

This Series illustrates the preparation and testing of supported rhodium iron catalysts. Reaction conditions were 300° C. and 1000 psi total pressure.

Preparation of Catalysts

Catalysts tested in this study were all prepared by essentially the same sequence of steps: An aqueous solution of soluble salts of both metals in the desired amounts was impregnated on the support; the impregnated support was carefully dried; the metal salt was reduced slowly in a flowing hydrogen atmosphere. When metal components were impregnated as nitrate salts, a pyrolysis step preceeded the hydrogen reduction step. In most cases, rhodium was impregnated as a $RhCl_3$ solution.

The description below illustrates this procedure for the catalyst used in Series A (rhodium and iron on Davison (TM) Grade 59 Silica Gel).

Rhodium trichloride and ferric chloride were dissolved in distilled water at ambient temperature. Davison Grade 59 Silica Gel (3–6 mesh) was placed in a vacuum flask. The top of the flask was sealed with a rubber septum, and the flask was evacuated through the side arm. A syringe needle was then used to inject the rhodium and iron solution onto the evacuated support with occasional shaking of the flask. When addition was complete, the impregnated support was allowed to stand at one atmosphere for ca. 30 minutes. It was then carefully dried in a nitrogen atmosphere: 80° C. (1 hr.); 110° C. (2 hrs.); 150° C. (2 hrs.). The dried, impregnated support was placed in a quartz tube through which hydrogen was continuously passed. The temperature was raised to 450° C. and held at that value for 2 hours. The reduced catalyst was cooled to ambient temperature in an atmosphere of flowing nitrogen.

Description of Test Reactor

The reactors used in these studies were bottom-agitated "Magnedrive" autoclaves as described in FIG. 1 of the paper by Berty, Hambrick, Malone and Ullock, entitled "Reactor for Vapor-Phase Catalytic Studies", presented as Preprint 42E at the Symposium on Advances in High-Pressure Technology—Part II, Sixty Fourth National Meeting of the American Institute of Chemical Engineers (AIChE), at New Orleans, Louisiana, on March 16–20, 1969 and obtainable from AIChE at 345 East 47 Street, New York, N.Y. 10017. A variable speed, externally driven fan continuously recirculated the reaction mixture over the catalyst bed. The autoclaves used in Series A and B were internally gold plated and the interior volume was about 400 cubic centimeters. The experiments of Series C were carried out in an unplated one gallon stainless steel autoclave. The following modifications were found to facilitate operation and inhibit run-away methanation reactions.

1. Hydrogen feed gas was introduced at the bottom of the autoclave through the well for the shaft of the Magnedrive agitator.
2. Carbon monoxide feed gas was introduced through a separate port at the bottom of the autoclave in order to avoid a hydrogen-rich zone in the autoclave. When carbon dioxide was fed, it was added with the carbon monoxide feed stream.

Experimental

Rhodium iron catalysts supported on silica gel were tested for synthesis activity in a backmixed autoclave described above. Reaction conditions and salient features of the product distribution are described in Table I below. In all cases, the feed gases included a quantity of carbon dioxide; the nominal level of carbon dioxide in the feed was 5% by volume. There was no indication that carbon dioxide had any effect on the activity or selectivity of any of the catalysts studied.

The following procedure was used in the Tests recited in the Table below. Carbon monoxide containing a few percent carbon dioxide, and hydrogen were fed to the reactor in the desired mole ratio from 4,500 psig headers. The carbon monoxide stream to the reactor was purified, using ⅛ inch activated carbon pellets which had been dried at 250° C. in a nitrogen flow overnight. One hundred eighty milliliters (ml) of catalyst was placed in the reactor in a perforated basket having a capacity of approximately 200 ml. The reactor was pressurized with hydrogen and the flows of carbon monoxide and hydrogen were adjusted to achieve the desired composition. During the pressurization of the reactor, the reactor temperature was adjusted to approximately 25° C. below that desired for that particular run.

The pressure and the temperature were then adjusted to the desired reaction condition. Approximately one hour was allowed for the reactor to come to a steady state before beginning to measure actual time of reaction. After one hour of reaction, a sample of liquid product was collected by cooling the product-containing gas through a brine condenser at 1500 psig and then trapping the liquid product in a series of four traps having a capacity of approximately one liter per trap. The traps were maintained in a low temperature bath containing a mixture of dry-ice and acetone. The liquid products from all the traps and the condenser were then combined to obtain a single liquid sample, which was then analyzed and the results reported in the Table below. The non-condensable gases were metered through a wet-test meter to determine the volume of gas, and a gas sample was collected to determine its composition.

Percent metal dispersion, as used herein, is defined as the percentage of metal atoms exposed on the catalyst surface as compared to the total number of metal atoms deposited. The percent metal dispersion was obtained by determining the chemisorption of carbon monoxide at room temperature on a clean metal catalyst surface, and then calculating the number of exposed surface atoms by assuming that one carbon monoxide molecule is chemisorbed per surface metal atom. These analytical procedures can be found in S. J. Gregg and K. S. W. Sing, *Adsorption Surface Area And Porosity*, where CO adsorption is described at pages 263–267 and the dynamic gas chromatographic technique is described at pages 339–343. The surface purity of the catalyst was measured by Auger Spectroscopic Analysis. The analysis of product and unreacted gases was accomplished by the use of gas chromatographic analysis of the various liquids and gases.

Results are presented in Table I below. (In this Table, as in others herein, a single test is frequently the average of two or more test runs.)

TABLE I

SELECTIVITY OF RHODIUM-IRON CATALYSTS[a]

| Test No. | Metal, % Rh | Metal, % Fe | Off Gas % CO | GHSV[b] | C Efficiency, % [c] Methane | Methanol | Acetaldehyde | Ethanol[e] | Acetic Acid[e] | Rate to $C_2$, lb/cf/hr[d] Acetaldehyde | Ethanol[e] | Acetic Acid[e] | Total |
|---|---|---|---|---|---|---|---|---|---|---|---|---|---|
| 1 | 5 | — | 50 | ca 4,000 | 37 | ca 0 | 24 | 16 | 20 | 5.7 | 3.8 | 4.7 | |
| 2 | — | 1.0 | 50 | 3,900 | 69 | 12 | .3 | 10 | .2 | ca 0 | 0.14 | ca 0 | 0.15 |
| 3 | 2.5 | 1.35 | 51 | 2,700 | 51 | 19 | 0.6 | 23 | .6 | .06 | 2.4 | .08 | 2.5 |
| 4 | 2.5 | 0.68 | 51 | 2,900 | 40 | 28 | 0.7 | 28 | 1.0 | .08 | 3.3 | 0.14 | 3.5 |
| 5 | 2.5 | 0.68 | 31 | 2,400 | 44 | 28 | 0.4 | 24 | 0.5 | 0.045 | 2.7 | 0.07 | 2.7 |

TABLE I-continued

SELECTIVITY OF RHODIUM-IRON CATALYSTS[a]

| | Metal, % | | Off Gas | | | | C Efficiency, %[c] | | | | Rate to $C_2$, lb/cf/hr[d] | | |
|---|---|---|---|---|---|---|---|---|---|---|---|---|---|
| Test No. | Rh | Fe | % CO | GHSV[b] | Methane | Methanol | Acetaldehyde | Ethanol[e] | Acetic Acid[e] | Acetaldehyde | Ethanol[e] | Acetic Acid[e] | Total |
| 6 | 2.5 | 0.68 | 66 | 3,000 | 44 | 20 | 1.0 | 30 | 1.3 | 0.065 | 2.0 | 0.12 | 2.2 |

[a] At 300° C. and 1000 psi. In all cases the catalyst support was Davison ɪᴍ Grade 59 silica gel.
[b] Approximate gaseous hourly space velocity: Volumes of reactant gas, measured at ambient conditions, fed to a unit volume of catalyst per hour.
[c] Percent carbon efficiency to a particular product is defined as: $100 \times \frac{\text{Number of moles of carbon present in the product}}{\text{Number of moles of CO converted to products other than } CO_2}$
[d] Units are pounds of indicated product produced per cu. ft. of catalyst per hour.
[e] Ethanol and acetic acid values include quantities present as ethyl esters and acetates.

SERIES B

This Series illustrates the employment of a somewhat higher temperature, 325° C. Results are presented in Table II below.

TABLE II

SELECTIVITY OF RHODIUM-IRON CATALYSTS[a]

| | Metal, % | | | Off Gas | | | C Efficiency, %[c] | | | | Rate to $C_2$, lb/cf/hr[d] | | |
|---|---|---|---|---|---|---|---|---|---|---|---|---|---|
| Test No. | Rh | Fe | GHSV[b] | % CO | Methane | Methanol | Acetaldehyde | Ethanol[e] | Acetic Acid[e] | Acetaldehyde | Ethanol[e] | Acetic Acid[e] | Total |
| 1 | 5 | — | 2,500 | 54 | 53 | ca 0 | 8 | 23 | 8.9 | 1.5 | 4.4 | 1.7 | 7.6 |
| 2 | 5 | — | 4,900 | 77 | 34 | ca 0 | 8 | 12 | 43 | .5 | .7 | 2.6 | 3.8 |
| 3 | — | 1.0 | 4,500 | 53 | 52 | 5.3 | 0.32 | 6.2 | 0.10 | 0.015 | 0.30 | 0.006 | 0.33 |
| 4 | — | 1.0 | 4,900 | 69 | 66 | 6.8 | 0.89 | 7.4 | 0.13 | 0.021 | 0.18 | 0.004 | 0.20 |
| 5 | 2.5 | 1.35 | 3,200 | 52 | 65 | 10 | 1 | 20 | 0.4 | 0.12 | 2.7 | 0.07 | 2.8 |
| 6 | 2.5 | 1.35 | 5,800 | 77 | 60 | 7 | 2.4 | 25 | 1.1 | 0.21 | 2.3 | 0.12 | 2.6 |
| 7 | 2.5 | 0.68 | 2,700 | 49 | 49 | 24 | .5 | 23 | .8 | 0.10 | 2.7 | .13 | 2.9 |
| 8 | 2.5 | 0.68 | 2,900 | 68 | 48 | 16 | 1.2 | 31 | 1.6 | 0.10 | 2.8 | .2 | 3.0 |

[a] At 325° C. and 1000 psi. In all cases the catalyst support was same as in Table I.
[b] through [e] are the same as in Table I.

SERIES C

This Series illustrates the use of higher pressures, namely 2500 psig, and similar temperature and space velocity.

Results are presented in Table III below.

TABLE III

SELECTIVITY OF RHODIUM-IRON CATALYSTS[a]

| | | | Metal, % | | | C Efficiency, %[c] | | | |
|---|---|---|---|---|---|---|---|---|---|
| Test No. | Off Gas % CO | GHSV[b] | Rh | Fe | Methane | Methanol | Acetaldehyde + Ethanol[e] | Acetic Acid[e] | Rate Total $C_2$[d] |
| 1 | 77 | 5,400 | 5.0[f] | — | 18 | 13 | 16 | 43 | 21 |
| 2 | 78 | 8,000 | 5.0[f] | — | 24 | 10 | 21 | 36 | 19 |
| 3 | 75 | 9,500 | 2.5[g] | 1.35 | 39 | 13 | 37 | 4.0 | 5.7 |
| 4 | 76 | 9,500 | 2.5[g] | 1.35 | 51 | 16 | 27 | 2.9 | 3.7 |
| 5 | 75 | 9,300 | 2.5[h] | 0.135 | 5.2 | 2.3 | 13 | 31 | 3.2 |
| 6 | 77 | 8,700 | 2.5[h] | 0.135 | 46 | 1.4 | 15 | 36 | 3.2 |
| 7 | 75 | 11,000 | 2.5[i] | — | 41 | 1.6 | 5.2 | 49 | 4.2 |
| 8 | 80 | 11,000 | 2.5[i] | — | 26 | 1.6 | 10 | 45 | 2.8 |

[a] At 325° C. and 2500 psi. Same catalyst support as in Table I.
[b] through [e] are same as in Table I.
[f] From $RhCl_3$. 22% dispersion.
[g] From $RhCl_3$. 19% dispersion.
[h] From $RhCl_3$. 2.7% dispersion. Iron from $Fe[(H_2O)_6]Cl_2$
[i] From $Rh(NO_3)$. 21% dispersion.

What is claimed is:

1. In a process for the reaction of a synthesis gas containing carbon monoxide and hydrogen in the presence of a hydrogenation catalyst, the improvement whereby oxygenated hydrocarbon products of two-carbon atoms are selectively produced, which comprises continuously contacting said synthesis gas with a heterogeneous catalyst consisting essentially of a combination of rhodium and iron and at reaction conditions correlated to achieve product efficiencies based on cabon consumption in excess of 10 percent and obtain the formation of ethanol, and optionally acetic acid and/or acetaldehyde as well, in an amount which is at least about 50 weight percent of the two or more carbon atom compounds obtained by the reaction and there is obtained an increased amount of ethanol relative to that produced when the catalyst is rhodium only, which reaction conditions include a temperature within the range of about 150°–450° C., a pressure within the range of about 15–10,000 psig, and a mole ratio of hydrogen to carbon monoxide within the range of 20:1 to 1:20.

2. Process of claim 1 wherein said reaction conditions include a temperature within the range of about 250°–350° C., a pressure within the range of about 300–5,000 psig, and a mole ratio of hydrogen to carbon monoxide within the range of about 5:1 to 1:5.

3. Process of claim 1 wherein said combination of rhodium and iron is present on a support in amounts within the range of about 0.1 to about 25 weight percent based on the combined weight of the metal and support.

4. Process of claim 1 wherein said support is selected from the group consisting of alpha alumina, gamma alumina, and silica gel.

5. Process of claim 1 wherein the space velocity of the synthesis gas is in excess of about $10^3$ GHSV.

6. Process of claim 5 wherein said space velocity is within the range of about $10^4$ to $10^6$ GHSV.

* * * * *

UNITED STATES PATENT AND TRADEMARK OFFICE
CERTIFICATE OF CORRECTION

PATENT NO. : 4,235,801
DATED : November 25, 1980
INVENTOR(S) : Madan M. Bhasin

It is certified that error appears in the above—identified patent and that said Letters Patent is hereby corrected as shown below:

At Column 6, line 60, at Table I under heading TOTAL results of Test No. 1 should read --14.2--.

Signed and Sealed this

Twelfth Day of February 1985

[SEAL]

Attest:

DONALD J. QUIGG

Attesting Officer     Acting Commissioner of Patents and Trademarks